United States Patent [19]

Gettings et al.

[11] Patent Number: 4,908,355

[45] Date of Patent: Mar. 13, 1990

[54] SKIN TREATMENT METHOD

[75] Inventors: Richard L. Gettings, Freeland; William C. White, Midland, both of Mich.

[73] Assignee: Dow Corning Corporation, Midland, Mich.

[21] Appl. No.: 294,724

[22] Filed: Jan. 9, 1989

[51] Int. Cl.$^4$ .......................................... A61K 31/695
[52] U.S. Cl. ............................................... 514/63
[58] Field of Search ........................................ 514/63

[56] References Cited

U.S. PATENT DOCUMENTS

| | | | |
|---|---|---|---|
| 3,541,205 | 11/1970 | Hardigan | 514/63 |
| 3,560,385 | 2/1971 | Roth | 252/49.6 |
| 3,730,701 | 5/1973 | Isquith et al. | 71/67 |
| 3,794,736 | 2/1974 | Abbott et al. | 424/78 |
| 3,817,739 | 6/1974 | Abbott et al. | 71/67 |
| 3,860,709 | 1/1975 | Abbott et al. | 424/184 |
| 3,865,728 | 2/1975 | Abbott et al. | 210/169 |
| 4,244,948 | 1/1981 | Bughosian | 424/230 |
| 4,259,103 | 3/1981 | Malek et al. | 71/67 |
| 4,282,366 | 8/1981 | Eudy | 556/413 |
| 4,371,577 | 2/1983 | Sato et al. | 428/96 |
| 4,394,378 | 7/1983 | Klein | 424/184 |
| 4,395,454 | 7/1983 | Baldwin | 428/290 |
| 4,406,892 | 9/1983 | Eudy | 424/184 |
| 4,408,996 | 10/1983 | Baldwin | 8/490 |
| 4,411,928 | 10/1983 | Baldwin | 427/2 |
| 4,414,268 | 11/1983 | Baldwin | 428/289 |
| 4,425,372 | 1/1984 | Baldwin | 427/2 |
| 4,467,013 | 8/1984 | Baldwin | 428/289 |
| 4,504,541 | 3/1985 | Yasuda et al. | 428/264 |
| 4,515,784 | 5/1985 | Bogardus | 514/63 |
| 4,536,399 | 8/1985 | Flynn | 514/63 |
| 4,564,456 | 1/1986 | Homan | 210/698 |
| 4,613,592 | 8/1986 | Benzoni | 514/63 |
| 4,615,937 | 10/1986 | Bouchette | 428/288 |
| 4,631,273 | 12/1986 | Blehm et al. | 514/29 |
| 4,631,297 | 12/1986 | Battice et al. | 521/78 |
| 4,692,374 | 9/1987 | Bouchette | 428/288 |
| 4,721,511 | 1/1988 | Kupits | 8/188 |
| 4,842,760 | 6/1989 | Blehm | 514/63 |
| 4,842,766 | 6/1989 | Blehm et al. | 514/63 |

FOREIGN PATENT DOCUMENTS

| | | | |
|---|---|---|---|
| 0160430 | 11/1985 | European Pat. Off. | 514/63 |
| 0119036 | 9/1979 | Japan | 514/63 |
| 0066506 | 5/1980 | Japan | 514/63 |
| 156809 | 3/1985 | Japan | 514/63 |
| 129186 | 6/1986 | Japan | 514/63 |
| 8601457 | 1/1987 | PCT Int'l Appl. | |
| 1386876 | 3/1975 | United Kingdom | |
| 1433303 | 4/1976 | United Kingdom | |
| 2144329 | 3/1985 | United Kingdom | 514/63 |

OTHER PUBLICATIONS

Applied Microbiology, vol. 24, No. 6, Dec. 1972, A. J. Isquith et al., "Surface Bonded Antimicrobial Activity of an Organosilicon Quaternary Ammonium Chloride".

*Primary Examiner*—Donald G. Daus
*Attorney, Agent, or Firm*—Jim L. DeCesare

[57] ABSTRACT

A method of treating skin disorders such as acne vulgaris by applying topically to the epidermis a composition of an emulsion in which there is present a silane and a volatile low viscosity low molecular weight water immiscible liquid of a silicone fluid, causing the silane to penetrate follicular orifices, using the volatile silicone fluid for the purpose of driving the silane into sebaceous glands, and destroying members of the staphylococcal group of bacteria therein. An abrasive, astringent, and fragrance may also be included. This method also allows for the treatment of dermatosis, such as ring worm and athlete's foot.

7 Claims, No Drawings

SKIN TREATMENT METHOD

BACKGROUND OF THE INVENTION

This invention relates to a method of treating skin disorders caused by transient as well as resident indigenant microorganisms which are present on the outer skin layer or extended downwardly into hair follicles, gland openings, and into the interior of glands.

An antimicrobial is an agent that destroys or inhibits the growth of microorganisms. The major classes of microorganisms are bacteria, fungi including mold and mildew, yeasts, and algae. Microorganisms can be found in the air, the waters, the human body, soil, wastes, and on all surfaces. The organisms are deposited from the air, food and drink spills, dust, dirt and tracked in soil, and from human excreta such as sweat, urine, and feces. Organisms grow and multiply when there is available a nutrient source of food such as dirt, organic or inorganic material, and living tissue. For growth and multiplication, organisms also require warm temperatures, and moisture. When these conditions exist, microorganisms thrive and flourish. Microbial growth, however, leads to many problems such as unpleasant odors ranging from stale to musty and mildew-like, to putrid and foul smelling, resembling ammonia. The growths also produce unsightly stains, discoloration, and deterioration of many surfaces and materials in which they come into contact. A more serious disadvantage of microbial growth is the production of pathogenic microorganisms, germs, their metabolic products and their somatic and reproductive cell parts, which contribute to the spread of disease, infection, and disorders.

Antimicrobial agents are chemical compositions that are used to prevent such microbiological contaminations by inhibiting, killing and/or removing them and neutralizing their effects of deterioration, defacement, odor, disease or other negative effects. Particular areas of application of antimicrobial agents and compositions are, for example, cosmetics, disinfectants, sanitizers, wood preservation, food, animal feed, cooling water, metalworking fluids, hospital and medical uses, plastics and resins, petroleum, pulp and paper, textiles, latex, adhesives, leather and hides, and paint slurries. In the area of medical applications, antimicrobials are often used as powders, in lotions, creams, ointments and/or delivered in a variety of solvents or directly as over-the-counter or ethical drugs to alleviate, mediate, cure and/or protect people or other animals from disease or cosmetic conditions. Of the diverse categories of antimicrobial agents and compositions, quaternary ammonium compounds represent one of the largest of the classes of antimicrobial agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. Silicone quaternary ammonium salt compounds are well known as exemplified by U.S. Pat. No. 3,560,385, issued February 2, 1971, and the use of such compounds as antimicrobial agents is taught, for example, in a wide variety of patents such as U.S. Pat. Nos. 3,730,701, issued May 1, 1973, and 3,817,739, issued June 18, 1974, where the compounds are used to inhibit algae; 3,794,736, issued February 26, 1974, and 3,860,709, issued January 14, 1975, where they are employed for sterilizing or disinfecting a variety of surfaces and instruments; and 3,865,728, issued February 11, 1975, where the compounds are used to treat aquarium filters. Published unexamined European application No. 228,464 of July 15, 1987, teaches that microorganisms on multi-cellular plants can be killed by the application thereto of an aqueous mixture of a surfactant and an organosilicon quaternary ammonium compound. U.S. Pat. No. 4,564,456, issued January 14, 1986, discloses organosilanes as anti-scale agents in water systems. In a particular application of an antimicrobial silicone quaternary ammonium compound, a paper substrate is rendered resistant to the growth of microorganisms in U.S. Pat. No. 4,282,366, issued August 4, 1981. In U.S. Pat. No. 4,504,541, issued March 12, 1985, an antimicrobial fabric is disclosed which is resistant to discoloration and yellowing by treatment of the fabric with a quaternary ammonium base containing an organosilicone. U.S. Pat. No. 4,615,937, issued October 7, 1986, as well as its companion U.S. Pat. No. 4,692,374, issued September 8, 1987, relate to wet wiper towelettes having an antimicrobial agent substantive to the fibers of the web and being an organosilicon quaternary ammonium compound. In a series of Burlington Industries, Inc. U.S. Pat. Nos. 4,408,996, issued October 11, 1983, 4,414,268, issued November 8, 1983, 4,425,372, issued January 10, 1984, and 4,395,454, issued July 26, 1983, such compounds are disclosed to be useful in surgical drapes, dressings, and bandages. This same assignee also discloses these compounds as being employed in surgeons' gowns in U.S. Pat. Nos. 4,411,928, issued October 25, 1983, and 4,467,013, issued August 21, 1984. Organosilicon quaternary ammonium compounds have been employed in carpets, in U.S. Pat. No. 4,371,577, issued February 1, 1983; applied to walls, added to paints, and sprayed into shoes, in U.S. Pat. No. 4,394,378, issued July 19, 1983; formulated as aqueous emulsions in U.S. Pat. No. 4,631,273, issued December 23, 1986; applied to polyethylene surfaces and used in pillow ticking in U.S. Pat. No. 4,721,511, issued January 26, 1988; in flexible polyurethane foams of fine-celled, soft, resilient articles of manufacture in U.S. Pat. No. 4,631,297, issued December 23, 1986; and mixed with a surfactant in British Pat. No. 1,386,876, of March 12, 1975, and in Japanese Kokai Application No. 58-156809, filed August 26, 1983, of Sanyo Chemical Industries, Ltd. Some general, more domestic type applications of these compounds, has included their use in a dentifrice as in U.S. Pat. No. 4,161,518 issued July 17, 1979; in a novel laundry detergent in U.S. Pat. No. 4,557,854, issued December 10, 1985; as a hair conditioner in U.S. Pat. No. 4,567,039, issued January 28, 1986; and in a soft contact lens disinfectant solution in U.S. Pat. No. 4,615,882, issued October 7, 1986. In U.S. Pat. No. 4,614,675, issued September 30, 1986, properties can be influenced by mixing the silicone quaternary ammonium salt compounds with certain siloxanes. Thus, the versatility of such compositions is readily apparent.

The prior art techniques for the treatment of acne have included compositions with an active ingredient such as benzoyl peroxide. Other methods have employed such active ingredients as sulfur, resorcinol, retinoic acid derivatives, and chlorohydroxy-quinoline. In U.S. Pat. No. 4,244,948, issued January 13, 1981, alkyl and aralkyl esters of acetylsalicylic acid are used in a topical acne treatment technique. It is not new to employ silicone compounds in skin treatment. For example, in U.S. Pat. No. 4,515,784, issued May 7, 1985, the spread of skin oil produced in the sebaceous glands is reduced by a composition applied topically that includes a high molecular weight polydimethylsiloxane polymer of molecular weight of about 330,000. Lower molecular weight materials are said to be not significant in the reduction of spreading of the skin oil.

Among the numerous attempts to alleviate the problems of microorganisms on skin surfaces have involved the use of soaps, detergents, and surface cleaners. The treatments, however, have for the most part included an unbound category of antimicrobial which is not actually bonded to the surface sought to be treated, and therefore is consumed by the microorganisms, with the result that the unbound antimicrobial is depleted and washed away during routine cleansing. As this diffusion continues, the concentration of the active ingredient becomes diluted below effective levels, with the result that the microorganisms sought to be inhibited, adapt and build up a tolerance, becoming immune to what was once an effective treatment dose. Such unbound diffusible antimicrobials have therefore been found to be limited in their ability to offer broad spectrum control of microorganisms, in contrast to the bound type of antimicrobial which remains chemically attached to the surface to which it is applied providing for a surface that prevents recolonization by the microflora associated therewith. Diffusing types of antimicrobials also often suffer from the propensity to transfer percutaneously, giving rise to sensitization and irritation immunological responses, and raising serious questions as to their ultimate fate within the body and body systems.

Bound antimicrobials kill organisms on contact and continue to kill organisms without being diffused or leached from the surface. Thus, the bound antimicrobial leaves behind an effective level of active ingredient and is able to control a broad spectrum of microorganisms including gram negative and gram positive bacteria, mold, mildew, fungi, yeast, and algae. An exemplary category of bound antimicrobial is an alkoxysilane quaternary ammonium compound, and such alkoxysilane quaternary ammonium compounds have been found to be more effective at reducing the number of microorganisms, and inhibiting microbially generated odors, than conventional organotin compounds and other organic quaternary ammonium compounds. The silanes of the present invention immobilize on surfaces and bond thereto to provide a coating of immobilized antimicrobial, unlike conventional materials.

In the present invention, this bound characteristic of alkoxysilane quaternary ammonium compounds, as well as their capabilities of performing at effective kill levels beyond prior art types of compositions, is taken advantage of in the treatment of skin disorders, in order to reduce or substantially eliminate the incidence of microorganisms, germs, their metabolic products and their somatic and reproductive cell parts, which contribute to the spread of such disorders.

SUMMARY OF THE INVENTION

This invention relates to a method of treating acne vulgaris of the skin by applying topically to the epidermis a composition of an emulsion including an antibacterially effective amount of a silane and a water immiscible liquid, causing the silane to penetrate follicular orifices, driving the silane into sebaceous glands, and destroying members of the staphylococcal group of bacterial therein. The silane is an organosilicon quaternary ammonium compound and an organosilane having the general formula selected from the group consisting of

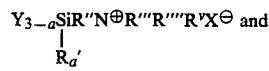

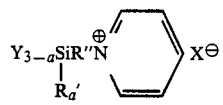

wherein, in each formula,

Y is R or RO where each R is an alkyl radical of 1 to 4 carbon atoms or hydrogen;

a has a value of 0, 1 or 2;

R′ is a methyl or ethyl radical;

R″ is an alkylene group of 1 to 4 carbon atoms;

R‴, R⁗ and $R^v$ are each independently selected from a group consisting of alkyl radicals of 1 to 18 carbon atoms, $-CH_2C_6H_5$, $-CH_2CH_2OH$, $-CH_2OH$, and $-(CH_2)_xNHC(O)R^{vi}$, wherein x has a value of from 2 to 10 and $R^{vi}$ is a perfluoroalkyl radical having from 1 to 12 carbon atoms; and X is chloride, bromide, fluoride, iodide, acetate or tosylate.

In a preferred embodiment, the water immiscible liquid is a polysiloxane selected from the group consisting of polysiloxanes having the general formula

wherein R′ is an alkyl radical of 1 to 3 carbon atoms, phenyl, an alkoxy radical having the formula R⁗O-, wherein R⁗ is an alkyl radical of 1 to 4 carbon atoms or hydrogen; R″ is an alkyl radical of 1 or 2 carbon atoms or the phenyl group; R‴ has the same meaning as R″; Q is a substituted or unsubstituted radical composed of carbon and hydrogen, or carbon, hydrogen and oxygen, or carbon, hydrogen and sulfur, or carbon, hydrogen and nitrogen; w has a value of from 1 to 500; z has a value of 1 to 25 and y has a value of 3 to 5.

The composition may also include an abrasive selected from the group consisting of pumice, talc, mica, iron oxide, titanium oxide, titanium dioxide, zinc oxide, kaolin, magnesium oxide, zinc stearate, magnesium stearate, starch, chalk, magnesium carbonate, and boric acid. In addition, a fragrance may be added to the composition, as well as an astringent selected from the group consisting of alum, silver nitrate, aluminum sulphate, aluminum chlorohydrate, zinc chloride, zinc chlorohydrate, aluminum-zirconium chlorohydrate, aluminum chlorohydroxide, zirconium hydroxychloride, aluminum hydroxychloride-zirconyl hydroxy oxychloride, and aluminum-zirconium tetrachlorohydrexglycinate. In one particularly preferred embodiment, the polysiloxane is selected from the group consisting of polydimethylsiloxane, polyphenylmethylsiloxane, and polydimethylcyclosiloxane. The compositions may take various forms ranging from emulsions and microemulsions to treated powders.

It is therefore an object of the present invention to provide a treatment method for skin disorders such as acne vulgaris in which an antimicrobial agent such as a bound type of silicone quaternary ammonium salt compound is caused to penetrate follicular openings of the skin areas sought to be treated whereby the antimicrobial agent actually enters within sebaceous glands in order to kill and immobilize microorganisms within the glands themselves of the Staphylococcus species of bacteria, for example. The driving force for causing the antimicrobial agent to penetrate downwardly within the sebaceous gland is provided by a highly volatile low viscosity low molecular weight silicone fluid such as siloxanes which are cyclics and polysiloxanes referred to hereinabove. These fluids carry the silicone quaternary ammonium antimicrobial compounds into contact with the bacteria which harbor within the regions of the gland, and hence, in addition to surface kill, provide an interior gland kill resulting in a more effective skin disorder treatment than known heretofore. Other penetrating assisting agents such as alcohols or dimethylformamide may also be used to assist in delivering the antimicrobial.

These and other features, objects, and advantages, of the present invention will be apparent when considered in light of the following detailed description thereof.

DETAILED DESCRIPTION OF THE INVENTION

Ammonium compounds in which all of the hydrogen atoms on nitrogen have been substituted by alkyl groups are called quaternary ammonium salts. These compounds may be represented in a general sense by the formula:

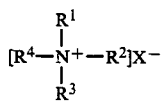

The nitrogen atom includes four covalently bonded substitutents that provide a cationic charge. The R groups can be any organic substituent that provides for a carbon and nitrogen bond with similar and dissimilar R groups. The counterion X is typically halogen. Use of quaternary ammonium compounds is based on the hydrophilic portion of the molecule which bears a positive charge. Since most surfaces are negatively charged, solutions of these cationic surface active agents are readily adsorbed to the negatively charged surface. This affinity for negatively charged surfaces is exhibited by 3-(trimethoxysilyl)propyldimethylocadecyl ammonium chloride of the formula:

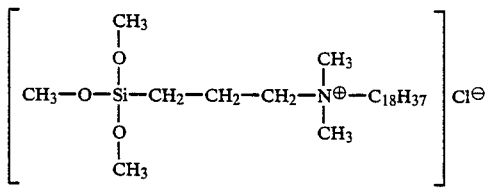

In the presence of moisture, this antimicrobial agent imparts a durable, wash resistant, broad spectrum biostatic surface antimicrobial finish to a substrate. The organosilicon quaternary ammonium compound is leach resistant, nonmigrating, and is not consumed by microorganisms. It is effective against gram positive and gram negative bacteria, fungi algae, yeasts, mold, rot, and mildew. The silicone quaternary ammonium salt provides durable, bacteriostatic, fungistatic, and algistatic surfaces. It can be applied to organic or inorganic surfaces as a dilute aqueous or solvent solution of 0.1–1.5 percent by weight of active ingredient. After the alkoxysilane is applied to a surface, it is chemically bonded to the substrate by condensation of the silanol groups at the surface. The pure compound is crystalline whereas methanol solutions of the compound are low viscosity, light to dark amber liquids, soluble in water, alcohols, ketones, esters, hydrocarbons, and chlorinated hydrocarbons. The compound has been used in applications such as, for example, socks, filtration media, bed sheets, blankets, bedspreads, carpet, draperies, fire hose fabric materials, humidifier belts, mattress pads, health care apparel, mattress ticking, underwear, nonwoven disposable diapers, nonwoven fabrics, outerwear fabrics, nylon hosiery, vinyl paper, wallpaper, polyurethane cushions, roofing materials, sand bags, tents, tarpaulins, sails, rope, blood pressure cuffs, athletic and casual shoes, shoe insoles, shower curtains, toilet tanks, toilet seat covers, throw rugs, towels, umbrellas, upholstery fiberfill, intimate apparel, wiping cloths, and medical devices such as blood pressure cuffs.

In the Examples as well as in the Tables, the composition identified as TMS refers to a product manufactured by the Dow Corning Corporation, Midland, Michigan, as an antimicrobial agent. This compound is 3-(trimethoxysilyl)-propyloctadecyldimethyl ammonium chloride referred to above diluted to forty-two percent active ingredients by weight with methanol.

The silanes useful in this invention have the general formula

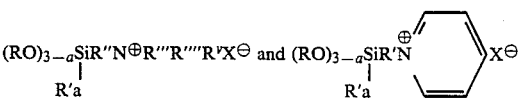

It should be noted that generically, these materials are quaternary ammonium salts of silanes. Most of the silanes falling within the scope of this invention are known silanes and references disclosing such silanes are numerous. One such reference, U.S. Pat. No. 4,259,103, issued to James R. Malek and John L. Speier, on March 31, 1981, discusses the use of such silanes to render the surfaces of certain substrates antimicrobial. British Pat. No. 1,433,303, issued to Charles A. Roth shows the use of fillers treated with certain silanes to be used in paints and the like to give antimicrobial effects.

Numerous other publications have disclosed such silanes, namely, A. J. Isquith, E. A. Abbott and P. A. Walters, Applied Microbiology, December, 1972, pages 859–863; P. A. Walters, E. A. Abbott and A. J. Isquith, Applied Microbiology, 25, No. 2, p. 253–256, February 1973 and E. A. Abbott and A. J. Isquith, U.S. Pat. No. 3,794,736 issued February 26, 1974, U.S. Pat. No. 4,406,892, issued September 27, 1983, among others.

For purposes of this invention, the silanes can be used neat or they can be used in solvent or aqueous-solvent solutions. When the silanes are used neat, the inventive process is preferably carried out in a system in which some small amount of water is present. If it is not possible to have a system with some small amount of water present, then a water soluble or water-dispersable, low molecular weight hydrolyzate of the silane may be used. What is important is the fact that the durability of any effect produced by the silane as part of a product requires that the silane molecule react with a surface to a certain extent. The most reactive species, as far as the silanes are concerned, is the ≡SiOH that is formed by hydrolysis of the alkoxy groups present on the silane. The ≡SiOH groups tend to react with the surface and bind the silanes to the surface. It is believed by the inventor that even though the prime mode of coupling to the surface system is by the route described above, it is also believed by the inventor that the alkoxy groups on the silicon atom may also participate in their own right to bind to the surface.

Preferred for this invention is a reactive surface containing some small amount of water. By "reactive", it is meant that the surface must contain some groups which will react with some of the silanols generated by hydrolysis of the silanes of this invention.

R in the silanes of this invention are alkyl groups of 1 to 4 carbon atoms. Thus, useful as R in this invention are the methyl, ethyl, propyl and butyl radicals. In the above formulas RO can also be R. R can also be hydrogen thus indicating the silanol form, i.e. the hydrolyzate. The value of a is 0, 1 or 2 and R' is a methyl or ethyl radical.

R'' for purposes of this invention is an alkylene group of 1 to 4 carbon atoms. Thus, R'' can be alkylene groups such as methylene, ethylene, propylene, and butylene. R''', R'''', and R$^v$ are each independently selected from a group which consists of alkyl radicals of 1 to 18 carbons, $-CH_2C_6H_5$, $-CH_2CH_2OH$, $-CH_2OH$, and $-(CH_2)_xNHC(O)R^{vi}$. x has a value of from 2 to 10 and R$^{vi}$ is a perfluoroalkyl radical having from 1 to 12 carbon atoms. X is chloride, bromide, fluoride, iodide, acetate or tosylate.

Preferred for this invention are the silanes of the general formula

 wherein

R is methyl or ethyl; a has a value of zero; R'' is propylene; R''' is methyl or ethyl; R'''' and R$^v$ are selected from alkyl groups containing 1 to 18 carbon atoms wherein at least one such group is larger than eight carbon atoms and x is either chloride, acetate or tosylate.

Most preferred for this invention are those silanes having the formula

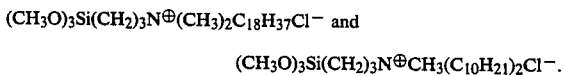

As indicated above, most of these silanes are known from the literature and methods for their preparation are known as well. See, for example, U.S. Pat. No. 4,282,366, issued August 4, 1981; U.S. Pat. No. 4,394,378, issued July 19, 1983, and U.S. Pat. No. 3,661,963 issued May 9, 1972, among others.

Specific silanes within the scope of the invention are represented by the formulae:

$(CH_3O)_3Si(CH_2)_3N^+(CH_3)_2C_{18}H_{37}Cl^-$,
$(CH_3O)_3Si(CH_2)_3N^+(CH_3)_2C_{18}H_{37}Br^-$,
$(CH_3O)_3Si(CH_2)_3N^+(C_{10}H_{21})_2CH_3Cl^-$,
$(CH_3O)_3Si(CH_2)_3N^+(C_{10}H_{21})_2CH_3Br^-$,
$(CH_3O)_3Si(CH_2)_3N^+(CH_3)_3Cl^-$,
$(CH_3O)_3SiCH_2CH_2CH_2P^+(C_6H_5)_3Cl^-$,
$(CH_3O)_3SiCH_2CH_2CH_2P^+(C_6H_5)_3Br^-$,
$(CH_3O)_3SiCH_2CH_2CH_2P^+(CH_3)_3Cl^-$,
$(CH_3O)_3SiCH_2CH_2CH_2P^+(C_6H_{13})_3Cl^-$,
$(CH_3)_3Si(CH_2)_3N^+(CH_3)_2C_{12}H_{25}Cl^-$,
$(CH_3)_3Si(CH_2)_3N^+(C_{10}H_{21})_2CH_3Cl^-$,
$(CH_3)_3Si(CH_2)_3N^+(CH_3)_2C_{18}H_{37}Cl^-$,
$(CH_3O)_3Si(CH_2)_3N^+(CH_3)_2C_4H_9Cl^-$,
$(C_2H_5O)_3Si(CH_2)_3N^+(CH_3)_2C_{18}H_{37}Cl^-$,
$(CH_3O)_3Si(CH_2)_3N^+(CH_3)_2CH_2C_6H_5Cl^-$,
$(CH_3O)_3Si(CH_2)_3N^+(CH_3)_2CH_2CH_2OHCl^-$,

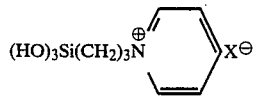

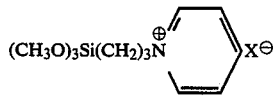

$(CH_3O)_3Si(CH_2)_3N^+(CH_3)_2(CH_2)_3NH-C(O)(CF_2)_6CF_3Cl^-$,
$(CH_3O)_3Si(CH_2)_3N^+(C_2H_5)_3Cl^-$.

The water immiscible liquids, or volatiles as used in the present invention, are silicone oils which are highly volatile, and low in viscosity and molecular weight. For example, there may be employed trimethylsiloxy endblocked polydimethylsiloxanes, cyclic siloxanes such as dimethylsiloxane cyclic tetramer, and phenylmethyl fluids such as linear polyphenylmethylsiloxanes. Preferred for this invention are those silicone oils having a viscosity at twenty-five degrees Centigrade ranging from about 0.65 cs to about one thousand cs. A particularly preferred range is from about 0.65 cs to about 20 cs, although those silicone oils of viscosities of 50 cs, and 350 cs, can be employed. These silicone oils are more particularly described and set forth in detail in U.S. Pat. No. 4,631,273, issued December 23, 1986, the disclosure of which is incorporated herein by reference. Such silicone oils are siloxanes which are low molecular weight cyclics and polysiloxanes having the general formula

wherein R' is an alkyl radical of 1 to 3 carbon atoms, phenyl, an alkoxy radical having the formula R''''O-, wherein R'''' is an alkyl radical of 1 to 4 carbon atoms or hydrogen; R'' is an alkyl radical of 1 or 2 carbon atoms or the phenyl group; R''' has the same meaning as R''; Q is a substituted or unsubstituted radical composed of carbon and hydrogen, or carbon, hydrogen and oxygen, or carbon, hydrogen and sulfur, or carbon, hydrogen and nitrogen; w has a value of from 1 to 500; z has a value of 1 to 25 and y has a value of 3 to 5.

As is well known, skin covers the human body and furnishes a protective covering for deeper tissues. It also serves as a barrier to prevent entry of infectious organisms which inhabit the skin surface. Skin performs important excretory functions by means of the sweat and sebaceous glands, and contains not only sweat and sebaceous glands but also hair follicles and sensory nerve endings of various kinds. The skin is made up of two layers including the deep or corium layer and the superficial or epidermis layer. The hairs are divided into the root and the shaft with the root being embedded in the hair follicle while the shaft is the free portion. Sebaceous glands exist wherever there are hairs. Ducts of the sebaceous glands open into the superficial parts of the hair follicles and vary in number for each follicle from one to four. The deep ends of the glands expand and contain droplets of oil which are liberated into the hair follicle. It is therefore possible for surface microorganisms to work their way downwardly through the follicular openings and into the sebaceous glands, gradually penetrating the expanded portion of the gland. It is these penetrating microorganisms, as well as those surface varieties, toward which the present invention is particularly directed.

Acne is any inflammatory disease of the sebaceous glands. Acne vulgaris is common acne and is a chronic inflammatory disease of the sebaceous glands seen most often on the face, back, and chest. The inflamed glands form small pink papules some of which surround comedones or blackheads or take the form of small pustules. Bacterial infections of the skin and its subjacent soft tissues may be generalized or localized, acute, subacute or chronic. Such infections are most often pyogenic and pus forming. The most frequent pyogenic infections including acne and acne vulgaris are caused by members of the Staphylococcal group of bacteria. Although many treatments of such diseases are known as noted hereinabove, none is known heretofore which will rid the sebaceous gland interiors of these Staphylococcal bacterial invaders. Thus, in accordance with the present invention, the water immiscible liquid, being highly volatile, carries the silane antimicrobial compound of the present invention downwardly into the interiors of the sebaceous glands wherein the bound antimicrobial compound kills or inhibits the proliferation of bacteria of the Staphylococcal group, as well as killing surface microorganisms. In combination with the water immiscible fluid, the antimicrobial agents of the present invention possess a penetrating power and permanence not heretofore known.

In the method of treating acne vulgaris in accordance with the present invention there is applied topically to the epidermis a composition of an emulsion including an antibacterially effective amount of a silane and a water immiscible liquid. The emulsion, its ingredients, and preparation, are disclosed in detail in U.S. Pat. No. 4,631,273, referred to above, and reference may be had thereto. The composition may also include in addition to the silane and water immiscible liquid, an abrasive selected from the group consisting of pumice, talc, mica, iron oxide, titanium oxide, titanium dioxide, zinc oxide, kaolin, magnesium oxide, zinc stearate, magnesium stearate, starch, chalk, magnesium carbonate, and boric acid. In addition, there may be included an astringent selected from the group consisting of alum, silver nitrate, aluminum sulphate, aluminum chlorohydrate, zinc chloride, zinc chlorohydrate, aluminum-zirconium chlorohydrate, aluminum chlorohydroxide, zirconium hydroxychloride, aluminum hydroxychloride-zirconyl hydroxy oxychloride, and aluminum-zirconium tetrachlorohydrex-glycinate.

The compositions of the present invention may include any type of fragrance, cologne, or perfume, compatible with the materials. For example, the fragrance may be a natural product such as Ambergris, Benzoin, Civet, Clove Leaf Oil, Galbanum, Jasmine Absolute, Labdanum, Mate', Melilot, Mimosa, Musk Tonquin, Myrrh, Mousse de Chene, Olibanum, Opopanax, Orris, Patchouli, Rosemary Oil, Sandalwood Oil, Vetivert Oil, and Violet Leaves Absolute. Among the various aroma chemicals that may be employed in addition to the foregoing natural products are, for example, acetylated cedarwood terpenes, amylcinnamic aldehyde, amyl salicylate, methyl salicylate, benzyl acetate, benzyl salicylate, p-tert-butylcyclohexyl acetate, citronellol, coumarin, Galaxolide, geraniol, hexylcinnamic aldehyde, isobornyl acetate, linalool, linalyl acetate, Lyral, musk ambrette, phenethyl alcohol, tetrahydromuguol, and terpinyl acetate. Fragrances that have become classics as descriptors for other fragrances in the same family are also included herein and would comprehend the Straight Floral Family, Floral Bouquet Family, Aldehydic Floral Family, Oriental Family, Chypre Family, Woody Family, Green Family, Citrus Family, Fougere Family, Canoe Family, Musk Family, Animal Family, Leather Family, Spice Family, and the Herbal Family.

Preferred fragrances include Citronellol, Cineole, YSL PARIS ®, manufactured by Charles of the Ritz Group of New York, New York; JOY ®, manufactured by Jean Patou, Inc. of New York, New York; OSCAR de la RENTA ®, manufactured by Oscar de la Renta, Ltd. of New York, New York; and IVOIRE de BALMAIN TM, manufactured by Balmain International B. V. of Rotterdam, Netherlands.

The following Example relates to a test conducted on carpet samples treated with TMS in order to show the efficacy of this antimicrobial agent against the bacterial microorganism *Staphylococcus aureus*.

EXAMPLE I

In order to demonstrate the effectiveness of TMS against the bacteria *Staphylococcus aureus*, nylon surfaces were treated with the antimicrobial agent, and the results are tabulated in Tables I to VIII. Comparisons were made on untreated as well as treated surfaces, in order to show the effect of TMS in inhibiting and inactivating test microbes applied to the surfaces. Four types of nylon material surfaces were selected for the tests, including a high-pile cut, a fine velour, a light loop fabric, and a heavy-duty loop fabric. Durability of treatment was shown by testing each surface type in its new condition, and after 7, 14, and 21, shampoo treatments. For the shampoo treatments, a commercial spray extraction device was used, and a non-bacterial shampoo having active groups of nonionic surfactants and phosphates. Each test was repeated three times in order to verify the results obtained.

Test surfaces 50 mm × 50 mm were used as microbe carrier. To prewet the surface, the surface was immersed at 37° C. into a phosphate buffer solution, removed, placed between sterile filter papers in order to remove excess fluid, and placed in sterile Petri dishes. Test microbes suspensions were obtained from a nutrient bouillon incubated for 18 hours at 37° C. and stirred at a frequency of 120 rpm by transferring 1 ml of culture bouillon into 9 ml of phosphate buffer. From this 1:10 dilution, a 1:100 dilution was made by placing 1 ml from the first dilution into 9 ml of phosphate buffer. Using the same procedure, a 1:1000 dilution of the suspension was formed. The 1:1000 dilution was used to inoculate the test pieces in sterile Petri dishes by applying 0.01 ml along each lateral edge and diagonally or a total of 0.05 ml of test microbial suspension per microbial carrier. The inoculated pieces were placed into sealed Petri dishes in an air-tight container which was filled to 10% of its volume with water and preheated to 37° C. Incubation of the test pieces was conducted at 37° C. in the container for 4 hours.

The microbial carrier was removed from the container and placed into covered glasses with 200 ml capacity and filled with 100 ml of Letheen broth, and shaken for 10 minutes on a shaking device with a frequency of 180 rpm. Reisolation of the test microbes was carried out by transferring 1 ml from the Letheen broth directly into a Petri dish followed by one dilution with Letheen broth 1:10 and 1:100. 1 ml of each of the dilutions was placed into a Petri dish and covered with microbial nutrient agar. The incubation time was 24 hours at 37° C. The grown colony forming units were then counted.

Results are shown in Tables I–VIII in logarithmic figures, and each Table refers to one piece of carpeting. The dilution stages are included so that a possible total microbial reduction is not expressed as such, but rather defined as "reduction>". In ascertaining reduction, the largest reduction value was selected from the absolute figures of the dilution stages of reisolation, converted into logarithms, and subtracted from the microbial seed. Treated carpet is durable since even the high number of shampooing treatments had no significant effect on the microbial reduction rates.

With high pile cut carpet an above-average inoculation with microbes such as *Staphylococcus aureus* led to reisolation of test microbes on microbial carriers treated with TMS. For fine velour, with *Staphylococcus aureus* on treated microbial carriers, the test microbe species were reisolated. The reduction rates in the microbial carriers of which *Staphylococcus aureus* was reisolated were above 4 log stages. The treated light loop fabric behaved as the fine velour. *Staphylococcus aureus* was reisolated on treated microbial carriers, and a microbial reduction of more than 4 log stages was established. *Staphylococcus aureus* was reisolated from the treated heavy-duty loop fabric. The microbial reduction rates for *Staphylococcus aureus* was between 3.85 and 3.91 log stages.

TABLE I

STAPHYLOCOCCUS AUREUS
MICROBIAL GROWTH REDUCTION OF TREATED AND UNTREATED HIGH-PILE CUT NYLON TEST SURFACES

| Shampoo Treatments | Legend | Untreated Run 1 | Untreated Run 2 | Untreated Run 3 | TMS Treated Run 1 | TMS Treated Run 2 | TMS Treated Run 3 |
|---|---|---|---|---|---|---|---|
| 0 | A | 6.47 | 6.32 | 6.25 | 6.47 | 6.32 | 6.25 |
|   | B | 4.30 | 4.06 | 3.98 | 2.60 | 2.30 | 2.00 |
|   | C | 2.17 | 2.26 | 3.27 | 3.87 | 4.02 | 4.25 |
| 7 | A | 5.91 | 5.86 | 5.76 | 5.91 | 5.86 | 5.76 |
|   | B | 4.04 | 4.03 | 3.99 | 2.30 | 2.30 | 2.00 |
|   | C | 1.87 | 1.83 | 1.77 | 3.61 | 3.56 | 3.76 |
| 14 | A | 5.66 | 5.59 | 5.62 | 5.66 | 5.59 | 5.62 |
|   | B | 3.86 | 3.76 | 3.37 | 2.47 | U | U |
|   | C | 1.80 | 1.83 | 1.83 | 3.19 | >3.59 | >3.62 |
| 21 | A | 5.81 | 5.77 | 5.69 | 5.81 | 5.77 | 5.69 |
|   | B | 3.99 | 3.93 | 3.91 | U | U | U |
|   | C | 1.82 | 1.84 | 1.78 | >3.81 | >3.77 | >3.69 |

A = Microbial inocculation
B = Reisolation
C = Reduction
U = No microbes reisolatable. Value below limit of detection of two-log stages.

TABLE II

STAPHYLOCOCCUS AUREUS
MICROBIAL GROWTH REDUCTION OF TREATED AND UNTREATED HIGH-PILE CUT NYLON TEST SURFACES

| Shampoo Treatments | A | Untreated Run 1 | Untreated Run 2 | Untreated Run 3 | TMS Treated Run 1 | TMS Treated Run 2 | TMS Treated Run 3 |
|---|---|---|---|---|---|---|---|
| 0 | B | 6.47 | 6.32 | 6.25 | 6.47 | 6.32 | 6.25 |
|   | 10-2 | 204 | 116 | 96 | 4 | 2 | 1 |
|   | 10-3 | 23 | 16 | 9 | 0 | 0 | 0 |
|   | 10-4 | 2 | 1 | 1 | 0 | 0 | 0 |
| 7 | B | 5.91 | 5.86 | 5.76 | 5.91 | 5.86 | 5.76 |
|   | 10-2 | 110 | 108 | 99 | 2 | 2 | 1 |
|   | 10-3 | 12 | 11 | 9 | 0 | 0 | 0 |
|   | 10-4 | 2 | 3 | 0 | 0 | 0 | 0 |
| 14 | B | 5.66 | 5.59 | 5.62 | 5.66 | 5.59 | 5.62 |
|   | 10-2 | 73 | 58 | 54 | 3 | 0 | 0 |
|   | 10-3 | 9 | 7 | 4 | 0 | 0 | 0 |
|   | 10-4 | 0 | 0 | 0 | 0 | 0 | 0 |
| 21 | B | 5.81 | 5.77 | 5.69 | 5.81 | 5.77 | 5.69 |
|   | 10-2 | 99 | 87 | 82 | 0 | 0 | 0 |
|   | 10-3 | 11 | 9 | 10 | 0 | 0 | 0 |
|   | 10-4 | 2 | 1 | 2 | 0 | 0 | 0 |

A = Microbial inocculation (log). Reisolation per microbial carrier in dilution stage.
B = Microbial inocculation

TABLE III

STAPHYLOCOCCUS AUREUS
MICROBIAL GROWTH REDUCTION OF TREATED AND UNTREATED NYLON FINE VELOUR TEST SURFACES

| Shampoo Treatments | Legend | Untreated Run 1 | Untreated Run 2 | Untreated Run 3 | TMS Treated Run 1 | TMS Treated Run 2 | TMS Treated Run 3 |
|---|---|---|---|---|---|---|---|
| 0 | A | 6.47 | 6.32 | 6.25 | 6.47 | 6.32 | 6.25 |
|   | B | 4.27 | 4.21 | 4.19 | 2.30 | 2.00 | 2.00 |
|   | C | 2.20 | 2.12 | 2.06 | 4.17 | 4.32 | 4.25 |
| 7 | A | 5.91 | 5.86 | 5.76 | 5.91 | 5.86 | 5.76 |
|   | B | 3.99 | 3.72 | 3.71 | U | U | U |
|   | C | 1.92 | 2.14 | 2.05 | >3.91 | >3.86 | >3.76 |
| 14 | A | 5.66 | 5.59 | 5.62 | 5.66 | 5.59 | 5.62 |
|   | B | 3.66 | 3.55 | 3.64 | U | U | U |
|   | C | 2.00 | 2.04 | 1.98 | >3.66 | >3.59 | >3.62 |
| 21 | A | 5.81 | 5.77 | 5.69 | 5.81 | 5.77 | 5.69 |
|   | B | 3.97 | 3.91 | 3.80 | U | U | U |
|   | C | 1.84 | 1.86 | 1.89 | >3.81 | >3.77 | >3.69 |

A = Microbial inocculation
B = Reisolation
C = Reduction
U = No microbes reisolatable. Value below limit of detection of two-log stages.

TABLE IV

STAPHYLOCOCCUS AUREUS
MICROBIAL GROWTH REDUCTION OF TREATED AND UNTREATED NYLON FINE VELOUR TEST SURFACES

| Shampoo Treatments | A | Untreated Run 1 | Untreated Run 2 | Untreated Run 3 | TMS Treated Run 1 | TMS Treated Run 2 | TMS Treated Run 3 |
|---|---|---|---|---|---|---|---|
| 0 | B | 6.47 | 6.32 | 6.25 | 6.47 | 6.32 | 6.25 |
|   | 10-2 | 188 | 163 | 156 | 2 | 1 | 1 |
|   | 10-3 | 16 | 14 | 14 | 0 | 0 | 0 |
|   | 10-4 | 1 | 1 | 1 | 0 | 0 | 0 |
| 7 | B | 5.91 | 5.86 | 5.76 | 5.91 | 5.86 | 5.76 |
|   | 10-2 | 98 | 53 | 52 | 0 | 0 | 0 |
|   | 10-3 | 11 | 6 | 7 | 0 | 0 | 0 |
|   | 10-4 | 0 | 0 | 0 | 0 | 0 | 0 |
| 14 | B | 5.66 | 5.59 | 5.62 | 5.66 | 5.59 | 5.62 |
|   | 10-2 | 46 | 36 | 44 | 0 | 0 | 0 |
|   | 10-3 | 3 | 3 | 2 | 0 | 0 | 0 |
|   | 10-4 | 0 | 0 | 0 | 0 | 0 | 0 |
| 21 | B | 5.81 | 5.77 | 5.69 | 5.81 | 5.77 | 5.69 |
|   | 10-2 | 94 | 83 | 64 | 0 | 0 | 0 |
|   | 10-3 | 11 | 7 | 7 | 0 | 0 | 0 |
|   | 10-4 | 2 | 0 | 0 | 0 | 0 | 0 |

A = Microbial inocculation (log). Reisolation per microbial carrier in dilution stage.
B = Microbial inocculation

TABLE V

STAPHYLOCOCCUS AUREUS
MICROBIAL GROWTH REDUCTION OF TREATED AND UNTREATED NYLON LIGHT LOOP FABRIC TEST SURFACES

| Shampoo Treatments | Legend | Untreated Run 1 | Run 2 | Run 3 | TMS Treated Run 1 | Run 2 | Run 3 |
|---|---|---|---|---|---|---|---|
| 0 | A | 6.47 | 6.32 | 6.25 | 6.47 | 6.32 | 6.25 |
|   | B | 4.09 | 4.03 | 3.96 | 2.30 | 2.30 | 2.00 |
|   | C | 2.38 | 2.29 | 2.29 | 4.17 | 4.17 | 4.25 |
| 7 | A | 5.91 | 5.86 | 5.76 | 5.91 | 5.86 | 5.76 |
|   | B | 3.94 | 3.82 | 3.77 | U | U | U |
|   | C | 1.97 | 2.04 | 1.99 | >3.91 | >3.86 | >3.76 |
| 14 | A | 5.66 | 5.59 | 5.62 | 5.66 | 5.59 | 5.62 |
|   | B | 3.66 | 3.56 | 3.61 | U | U | U |
|   | C | 2.00 | 2.03 | 2.01 | >3.66 | >3.59 | >3.62 |
| 21 | A | 5.81 | 5.77 | 5.69 | 5.81 | 5.77 | 5.69 |
|   | B | 3.69 | 3.66 | 3.59 | U | U | U |
|   | C | 2.12 | 2.11 | 2.10 | >3.81 | >3.77 | >3.69 |

A = Microbial inocculation
B = Reisolation
C = Reduction
U = No microbes reisolatable. Value below limit of detection of two-log stages.

TABLE VI

STAPHYLOCOCCUS AUREUS
MICROBIAL GROWTH REDUCTION OF TREATED AND UNTREATED NYLON LIGHT LOOP FABRIC TEST SURFACES

| Shampoo Treatments | A | Untreated Run 1 | Run 2 | Run 3 | TMS Treated Run 1 | Run 2 | Run 3 |
|---|---|---|---|---|---|---|---|
| 0 | B | 6.47 | 6.32 | 6.25 | 6.47 | 6.32 | 6.25 |
|   | 10-2 | 125 | 108 | 93 | 2 | 2 | 1 |
|   | 10-3 | 19 | 14 | 12 | 0 | 0 | 0 |
|   | 10-4 | 3 | 0 | 2 | 0 | 0 | 0 |
| 7 | B | 5.91 | 5.86 | 5.76 | 5.91 | 5.86 | 5.76 |
|   | 10-2 | 88 | 67 | 59 | 0 | 0 | 0 |
|   | 10-3 | 12 | 8 | 4 | 0 | 0 | 0 |
|   | 10-4 | 2 | 0 | 0 | 0 | 0 | 0 |
| 14 | B | 5.66 | 5.59 | 5.62 | 5.66 | 5.59 | 5.62 |
|   | 10-2 | 46 | 37 | 41 | 0 | 0 | 0 |
|   | 10-3 | 5 | 2 | 4 | 0 | 0 | 0 |
|   | 10-4 | 0 | 0 | 0 | 0 | 0 | 0 |
| 21 | B | 5.81 | 5.77 | 5.69 | 5.81 | 5.77 | 5.69 |
|   | 10-2 | 49 | 46 | 39 | 0 | 0 | 0 |
|   | 10-3 | 6 | 7 | 4 | 0 | 0 | 0 |
|   | 10-4 | 0 | 0 | 0 | 0 | 0 | 0 |

A = Microbial inocculation (log). Reisolation per microbial carrier in dilution stage.
B = Microbial inocculation

TABLE VII

STAPHYLOCOCCUS AUREUS
MICROBIAL GROWTH REDUCTION OF TREATED AND UNTREATED NYLON HEAVY-DUTY LOOP FABRIC TEST SURFACES

| Shampoo Treatments | Legend | Untreated Run 1 | Run 2 | Run 3 | TMS Treated Run 1 | Run 2 | Run 3 |
|---|---|---|---|---|---|---|---|
| 0 | A | 6.47 | 6.32 | 6.25 | 6.47 | 6.32 | 6.25 |
|   | B | 3.97 | 3.91 | 3.74 | 2.60 | 2.47 | U |
|   | C | 2.50 | 2.41 | 2.51 | 3.87 | 3.85 | >4.25 |
| 7 | A | 5.91 | 5.86 | 5.76 | 5.91 | 5.86 | 5.76 |
|   | B | 3.98 | 3.96 | 3.64 | 2.00 | 2.00 | U |
|   | C | 1.93 | 1.90 | 1.92 | 3.91 | 3.86 | >3.76 |
| 14 | A | 5.66 | 5.59 | 5.62 | 5.66 | 5.59 | 5.62 |
|   | B | 3.83 | 3.74 | 3.79 | U | U | U |
|   | C | 1.83 | 1.85 | 1.83 | >3.66 | >3.59 | >3.62 |
| 21 | A | 5.81 | 5.77 | 5.69 | 5.81 | 5.77 | 5.69 |
|   | B | 3.83 | 3.79 | 3.59 | U | U | U |
|   | C | 1.98 | 1.98 | 2.10 | >3.81 | >3.77 | >3.81 |

A = Microbial inocculation
B = Reisolation
C = Reduction
U = No microbes reisolatable. Value below limit of detection of two-log stages.

TABLE VIII

STAPHYLOCOCCUS AUREUS
MICROBIAL GROWTH REDUCTION OF TREATED AND UNTREATED NYLON HEAVY-DUTY LOOP FABRIC TEST SURFACES

| Shampoo Treatments | A | Untreated Run 1 | Run 2 | Run 3 | TMS Treated Run 1 | Run 2 | Run 3 |
|---|---|---|---|---|---|---|---|
| 0 | B | 6.47 | 6.32 | 6.25 | 6.47 | 6.32 | 6.25 |
|   | 10-2 | 94 | 83 | 56 | 4 | 3 | 0 |
|   | 10-3 | 11 | 9 | 7 | 0 | 0 | 0 |
|   | 10-4 | 2 | 2 | 0 | 0 | 0 | 0 |
| 7 | B | 5.91 | 5.86 | 5.76 | 5.91 | 5.86 | 5.76 |
|   | 10-2 | 96 | 93 | 44 | 1 | 1 | 0 |
|   | 10-3 | 13 | 11 | 5 | 0 | 0 | 0 |
|   | 10-4 | 2 | 1 | 0 | 0 | 0 | 0 |
| 14 | B | 5.66 | 5.59 | 5.62 | 5.66 | 5.59 | 5.62 |
|   | 10-2 | 68 | 56 | 62 | 0 | 0 | 0 |
|   | 10-3 | 7 | 7 | 8 | 0 | 0 | 0 |
|   | 10-4 | 0 | 0 | 0 | 0 | 0 | 0 |
| 21 | B | 5.81 | 5.77 | 5.69 | 5.81 | 5.77 | 5.69 |
|   | 10-2 | 69 | 62 | 39 | 0 | 0 | 0 |
|   | 10-3 | 9 | 7 | 5 | 0 | 0 | 0 |
|   | 10-4 | 1 | 0 | 0 | 0 | 0 | 0 |

A = Microbial inocculation (log). Reisolation per microbial carrier in dilution stage.
B = Microbial inocculation The anion of an aqueous sodium salt of bromphenol blue can be complexed with the cation of polymerized silanes of this invention while on a substrate. The blue colored complex, substantive to a water rinse, is qualitatively indicative of the presence of the cation on the substrate thus indicating the extent of antimicrobial agent on a given substrate. A comparison of the intensity of retained blue color to a color standard is used as a check to determine if the treatment has been applied properly.

One method consists of preparing a 0.02 to 0.04 weight percent solution of bromphenol blue in distilled water. This solution is made alkaline using a few drops of saturated $Na_2CO_3$ solution per 100 milliliters of the solution. Two to three drops of this solution are placed on the treated substrate and allowed to stand for two minutes. The substrate is then rinsed with copious amounts of tap water and the substrate is observed for a blue stain and it is compared to a color standard.

For a spectrophotometric determination, the following test is used. The sodium salt of bromphenol blue is depleted from a standard solution by complexing with the cations on a treated substrate. The change in bromphenol blue concentration is determined spectrophotometrically or by comparison with color standards whereby the level of substrate treatment by the cationic silane is determinable.

The method consists of preparing a 0.02 weight percent standard solution of bromphenol blue in distilled water. It is made alkaline with a few drops of saturated Na$_2$CO$_3$ solution per 100 milliliters of bromphenol blue solution. The color of this solution is purple. The blank solution is adjusted to yield a 10 to 12% transmittance reading when measured in 1 cm cells using a spectrophotometer set at 589 nm by the following method. Fill a container ¾ full of distilled water and add 2 ml of the 0.02% standard bromphenol blue solution for every 50 ml of distilled water. Add 0.5 ml of a 1% Triton ® X-100 surfactant (manufactured by Rohm and Haas, Philadelphia, PA, USA) aqueous solution for every 50 ml of water. Mix, and using the spectrophotometer, determine the maximum absorbance. Adjust the upper zero to 100% transmittance with distilled water. Check the percent transmittance of the working bromphenol blue solution at the maximum absorbance setting. Adjust the blank solution to 10 to 12% transmittance with either water or bromphenol blue standard solution as necessary.

The samples of treated substrate can be tested by placing 0.5 gram samples of the substrate standards in a flask large enough for substantial agitation of the sample and the test solution. Add 50 ml of the working solution. Agitate for 20 minutes on a wrist-action shaker. Fill the test curvette with the test solution. Centrifuge if particulate matter is present. Measure the % transmittance at the wavelength set forth above. The transmittance is compared against a standard curve prepared by preparing several substrate samples of known concentration of the cationic silane. For example, samples containing a known amount of cationic silane at, for example, 0%, 0.25%, 0.50%, 0.75% and 1% are read spectrophotometrically and a curve is plotted.

The antimicrobial activity of a treated surface is normally evaluated by shaking a sample weighing 0.75 grams in a 750,000 to 1,500,000 count *Klebsiella pneumoniae* suspension for a one hour contact time. The suspension is serially diluted, both before and after contact, and cultured. The number of viable organisms in the suspensions is determined. The percent reduction based on the original count is determined. The method is intended for those surfaces having a reduction capability of 75 to 100% for the specified contact time. The results are reported as the percent reduction. Media used in this test are nutrient broth, catalog No. 0003-01-6 and tryptone glucose extract agar, catalog No. 0002-01-7 both available from Difco Laboratories, Detroit, Michigan, U.S.A. The microorganism used is *Klebsiella pneumoniae* American Type Culture Collection; Rockville, Md. U.S.A., catalog No. 4352. The procedure used for determining the zero contact time counts is carried out by utilizing two sterile 250 ml. screw-cap Erlenmeyer flasks for each sample. To each flask is added 70 ml of sterile buffer solution. To each flask is added, aseptically, 5 ml of the organism inoculum. The flasks are capped and placed on a wrist action shaker. They are shaken at maximum speed for 1 minute. Each flask is considered to be at zero contact time and is immediately subsampled by transferring 1 ml of each solution to a separate test tube containing 9 ml of sterile buffer. The tubes are agitated with a vortex mixer and then 1 ml of each solution is transferred to a second test tube containing 9 ml of sterile buffer. Then, after agitation of the tubes, 1 ml of each tube is transferred to a separate sterile petri dish. Duplicates are also prepared. Sixteen ml of molten (42° C.) tryptone glucose extract agar is added to each dish. The dishes are each rotated ten times clockwise and ten times counterclockwise. The dishes are then incubated at 37° C. for 24 to 36 hours. The colonies are counted considering only those between 30 and 300 count as significant. Duplicate samples are averaged. The procedure used for determining the bacterial count after 1 hour is essentially the same as that used to determine the count at the zero contact time. The only difference is that pour plating is performed at the 10$^0$ and 10$^{-1}$ dilutions as well as at the 10$^{-2}$ dilution. "Percent reduction" is calculated by the formula $$\%R = \frac{\frac{B+C}{2} - A_{100}}{\frac{B+C}{2}}$$

where A is the count per milliliter for the flask containing the treated substrate; B is zero contact time count per milliliter for the flask used to determine "A" before the addition of the treated substrate and C is zero contact time count per milliliter for the untreated control substrate.

EXAMPLE II

Antimicrobial activity against common skin isolates was determined using TMS coated (0.42% by weight) orlon nylon fabric. Evaluations were done using American Association of Textile Chemists and Colorists - 100-1977 test. Four swatches of test fabric were placed in the bottom of a milk dilution bottle; one ml of a 1×10$^5$–5×10$^5$/ml titer of the test organisms were padded onto the test fabrics; the test bottle was incubated for six hours at 37° C.; a neutralizing (Letheen broth) recovery solution was added, shaken; standard pour plate counts made using tryptic soy agar; incubated at 37° C. for 18–20 hours; and standard counts were made. Percent reductions were calculated as compared to the organisms retrieved from untreated orlon nylon fabric. Significant reduction of all test bacteria is demonstrated with up to five logs of reduction demonstrated, as seen in Table IX.

TABLE IX

| TMS ACTIVITY AGAINST SKIN ISOLATES | | |
|---|---|---|
| Skin Isolated Test Organism | Gram Stain | % Bacterial Reduction |
| *Micrococcus sp.* (I) | + | 99.0 |
| *Staphylococcus epidermidis* | + | 96.4 |
| *Enterobacter aglomerans* (I) | − | 90.6 |
| *Acinetobacter calcoaceticus* | − | 99.9 |
| *Enterobacter aglomerans* (II) | − | 69.0 |
| *Micrococcus sp.* (II) | + | 100.0 |
| *Micrococcus sp.* (III) | + | 99.9 |
| *Staphylococcus aureus* (pigmented) | + | 99.9 |
| *Staphylococcus aureus* (nonpigmented) | + | 99.9 |

EXAMPLE III

To demonstrate applicability and durability to the skin, volunteers were used. TMS as a 0.42% water solution (A); TMS (14.4%) as the emulsifier of a volatile silicone in water diluted to 0.42% active in water (B); TMS (14.4%) as the emulsifier of polydimethylsilicone (PDMS), 50 centistokes, diluted to 0.42% active in water (C); and a water control (D); were swabbed onto the back of the left hand progressing up the anterior forearm as A, B, C, and D of each test subject, and allowed to air dry. Each test patch was approximately 3 cm by 6 cm. After drying, successive tape pulls of Scotch® Brand Magic™ Tape were made, and colorimetric analyticals made by dipping the test tapes in a 0.25% Bromophenol blue solution for five minutes at ambient room temperature; rinsed in water; and dried. Readings were made based on bromophenol blue intensity on the tape. Affinity for and durability of TMS to the skin is demonstrated with greater penetration provided by the PDMS fluid, and the greatest penetration by the volatile fluid preparation of the present invention.

The results of Example III are shown in Table X.

TABLE X

| | SKIN DURABILITY - TMS | | | | | | | | | | | | | | | | | | | |
|---|---|---|---|---|---|---|---|---|---|---|---|---|---|---|---|---|---|---|---|---|
| | Formulation/Tape Pull/Ratings | | | | | | | | | | | | | | | | | | | |
| | A. TMS Water BPB Rating 1, 2 Pulls | | | | | B. TMS Volatile BPB Rating Pulls | | | | | C. TMS PDMS BPB Rating Pulls | | | | | D. Water Control BPB Rating Pulls | | | | |
| Subject | 1 | 2 | 3 | 4 | 5 | 1 | 2 | 3 | 4 | 5 | 1 | 2 | 3 | 4 | 5 | 1 | 2 | 3 | 4 | 5 |
| 1. Male | H | H | L | O | O | H | H | H | M | L | H | H | M | L | O | O | O | O | O | O |
| 2. Male | H | H | L | L | O | H | H | H | M | L | H | M | M | O | O | O | O | O | O | O |
| 3. Female | H | H | L | O | O | H | H | H | L | L | H | M | M | O | O | O | O | O | O | O |
| 4. Female | H | H | L | O | O | H | H | H | L | L | H | M | M | O | O | O | O | O | O | O |

1. BPB - Bromophenol Blue
2. H = Very Dark Blue
M = Medium Blue
L = Light Blue
O = No Color

EXAMPLE IV

Antimicrobial activity against the organism associated with acne vulgaris, *Propionibacterium acnes*, was determined as follows. *P. acnes* was applied to Dacron fabrics that had been surface treated with the compositions A-D of Example III above.

The test compositions with TMS were swab applied to saturation on a 8 cm × 8 cm swatch of Dacron, dried at 100° C. for 15 minutes, and tested using the American Association of Textile Chemists and Colorists - 100-1977 test, modified to include retrieval media suitable for growing the *P. acnes*. The results are indicated in Table XI.

TABLE XI

| | TMS COATED FABRICS AGAINST PROPIONIBACTERIUM ACNES | | | |
|---|---|---|---|---|
| Sample | A. TMS Water On Fabric | B. TMS Volatile On Fabric | C. TMS PDMS On Fabric | D. Water Control On Fabric |
| % Reduction P. acnes | 99.99 | 99.96 | 99.98 | 0 |

In Examples II to IV and in Tables IX to XI, the term "volatile" has been used to indicate those materials previously indicated as the water immiscible liquids, and PDMS is a fifty centistoke polydimethylsiloxane fluid, measured at 25° C.

The foregoing illustrates the activity of the compounds of the present invention. Such compounds have been found to be effective against a number of microorganisms, such as BACTERIA: Gram (−): *Escherichia coli, Klebsiella pneumoniae, Klebsiella oxytoca, Pseudomonas aeruginosa, Pseudomonas fluorescens, Proteus mirabilis, Proteus vulgaris, Salmonella typhi, Salmonella typhimurium, Salmonella cholera suis, Enterobacter cloacae, Enterobacter aerogenes, Morganella morganii, Aeromonas hydrophila, Citrobacter freundii, Citrobacter deversus, Serratia marcescens, Serratia liquifaciens, Xanthomonas campestris, Acinetobacter calcoaceticus*; Gram (+): *Staphylococcus aureus, Staphylococcus epidermidis, Streptococcus mutans, Streptococcus pyogenes, Streptococcus fecalis, Micrococcus lutea*, Bacillus sp. (vegetative cell); Fungi: *Aspergillus niger, Aspergillus flavus, Aspergillus sydowi, Aspergillus versicolor, Aspergillus terreus, Penicillium chrysogenum, Penicillium variabile, Penicillium funiculosum, Penicillium pinophilum, Poria placenta, Aureobasidium pullulans, Gloeophyllum trabeum, Chaetomium globosum, Trichoderma viride, Trichophyton mentagrophytes*; Fungi (yeasts): *Candida albicans, Candida pseudotropicalis, Saccharomyces cerevisiae*.

The treatment of skin disclosed herein can be carried out with the quaternary ammonium compounds of this invention per se. Often, however, it is desirable to extend the compounds of this invention by incorporating therein hydrocarbon or halohydrocarbon substituted siloxanes of the formula

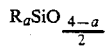

in which R is a hydrocarbon or halohydrocarbon radical and a varies from 0 to 3. The incorporation of such siloxanes in no way effects the property of the quaternary ammonium compound so that the claims of this invention are construed to cover both the use of quaternary ammonium siloxane per se and mixtures or copolymers of such siloxanes with said hydrocarbon substituted siloxanes or halohydrocarbon substituted siloxanes.

For example, surfaces can be treated with an aqueous solution of a mixture of 10 mols of monomethyl trimethysilane and 1 mol of

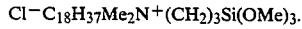

It has also been found that combinations of 1 mol

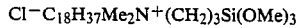

and 0.5 mol of 3-chloropropyltrimethoxysilane give effective siloxane coatings. The use of hydrocarbon and halohydrocarbon siloxane extenders often give cheaper, more durable, more oleophilic or oleophobic surface treatments, than the pure quaternary siloxane.

It will be apparent from the foregoing that many other variations and modifications may be made in the compounds, compositions, and methods described herein without departing substantially from the essential features and concepts of the present invention. Accordingly, it should be clearly understood that the forms of the invention described herein are exemplary only and are not intended as limitations on the scope of the present invention.

That which is claimed is:

1. A method of treating acne vulgaris comprising applying topically to the epidermis a mixture of an antibacterially effective amount of a silane and a water immiscible liquid, the silane being an organosilicon quaternary ammonium compound and an organosilane having the formula selected from the group consisting of

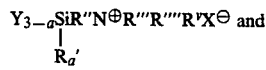 and

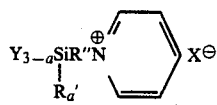

wherein, in each formula,

Y is R or RO where each R is an alkyl radical of 1 to 4 carbon atoms or hydrogen;

a has a value of 0, 1 or 2; R' is a methyl or ethyl radical;

R" is an alkylene group of 1 to 4 carbon atoms;

R''', R'''' and $R^v$ are each independently selected from a group consisting of alkyl radicals of 1 to 18 carbon atoms, $-CH_2C_6H_5$, $-CH_2CH_2OH$, $-CH_2OH$, and $-(CH_2)_xNHC(O)R^{vi}$, wherein x has a value of from 2 to 10 and $R^{vi}$ is a perfluoroalkyl radical having from 1 to 12 carbon atoms; and X is chloride, bromide, fluoride, iodide, acetate or tosylate, the water immiscible liquid being a polysiloxane having the formula $(R'R''SiO)_y$ wherein R' is an alkyl radical of 1 to 3 carbon atoms; R" is an alkyl radical of 1 or 2 carbon atoms; and y has a value of 3 to 5.

2. The method of claim 1 wherein the composition includes an abrasive selected from the group consisting of pumice, talc, mica, iron oxide, titanium oxide, titanium dioxide, zinc oxide, kaolin, magnesium oxide, zinc stearate, magnesium stearate, starch, chalk, magnesium carbonate, and boric acid.

3. The method of claim 2 wherein the composition includes an astrigent selected from the group consisting of alum, silver nitrate, aluminum sulphate, aluminum chlorohydrate, zinc chloride, zinc chlorohydrate, aluminum-zirconium chlorohydrate, aluminum chlorohydroxide, zirconium hydroxychloride, aluminum hydroxychloride-zirconyl hydroxy oxychloride, and aluminum-zirconium tetrachlorohydrex-glycinate.

4. The method of claim 3 wherein the composition includes a fragrance.

5. The method of claim 4 wherein the polysiloxane is polydimethylcyclosiloxane.

6. A method as claimed in claim 1 wherein the organosilicon compound has the formula

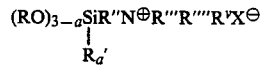

wherein each R is an alkyl radical of 1 to 4 carbon atoms or hydrogen; a has a value of 0,1 or 2; R' is a methyl or ethyl radical; R" is an alkylene group of 1 to 4 carbon atoms; R''', R'''' and $R^v$ are each independently selected from a group consisting of alkyl radicals of 1 to 18 carbon atoms, $-CH_2C_6H_5$, $-CH_2CH_2OH$, $-CH_2OH$, and $-(CH_2)_xNHC(O)R^{vi}$, wherein x has a value of from 2 to 10 and $R^{vi}$ is a perfluoroalkyl radical having from 1 to 12 carbon atoms; X is chloride, bromide, fluoride, iodide, acetate or tosylate.

7. A method as claimed in claim 1 wherein the organosilicon compound has the formula

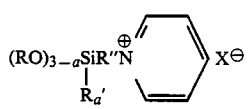

wherein R is an alkyl radical of 1 to 4 carbon atoms or hydrogen; a has a value of 0, 1 or 2; R' is a methyl or ethyl radical; R" is an alkylene of 1 to 4 carbon atoms; X is chloride, bromide, fluoride, iodide, acetate or tosylate.

* * * * *